US008682043B2

(12) United States Patent
Cahill et al.

(10) Patent No.: US 8,682,043 B2
(45) Date of Patent: Mar. 25, 2014

(54) METHOD OF MERGING ANATOMICAL DATA AND SURFACE DATA OF A PATIENT'S DENTITION

(75) Inventors: Sean B. Cahill, Temecula, CA (US); Shaun (Shahram) Zamani, San Diego, CA (US); Suneel Ranga Sai Battula, San Diego, CA (US); Steve T. Pelote, Vista, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 970 days.

(21) Appl. No.: 12/393,624

(22) Filed: Feb. 26, 2009

(65) Prior Publication Data

US 2009/0220134 A1    Sep. 3, 2009

Related U.S. Application Data

(60) Provisional application No. 61/032,506, filed on Feb. 29, 2008.

(51) Int. Cl.
*G06K 9/46* (2006.01)

(52) U.S. Cl.
USPC .............. 382/128; 433/29; 433/196; 433/214

(58) Field of Classification Search
USPC ............................. 382/128; 433/29, 196, 214
See application file for complete search history.

(56) References Cited

U.S. PATENT DOCUMENTS

| 4,611,288 | A | * | 9/1986 | Duret et al. .................... 700/163 |
| 5,365,996 | A | | 11/1994 | Crook |
| 5,702,128 | A | | 12/1997 | Maxim et al. |
| 5,725,376 | A | | 3/1998 | Poirier |
| 5,768,134 | A | | 6/1998 | Swaelens et al. |
| 6,925,198 | B2 | | 8/2005 | Scharlack et al. |
| 7,362,890 | B2 | | 4/2008 | Scharlack et al. |
| 7,574,025 | B2 | | 8/2009 | Feldman |
| 2006/0072810 | A1 | | 4/2006 | Scharlack et al. |
| 2006/0293760 | A1 | * | 12/2006 | DeDeyne ................... 623/23.76 |

(Continued)

OTHER PUBLICATIONS

Article "The Evolution of Multiplanar Diagnostic Imaging: Predictable Transfer of Preoperative analysis to the Surgical Site" Lewis S. Benjamin, DMD, MS, Journal of Oral Implantology vol. XXVIII/No. Three/2002, pp. 135-144.

*Primary Examiner* — Wensing Kuo
(74) *Attorney, Agent, or Firm* — Schwegman Lundberg & Woessner, P.A.

(57) ABSTRACT

A method of obtaining and merging volumetric data and surface data of a patient's dentition for use in designing and/or manufacturing a prosthodontic component, such as a drill guide, an implant, or other prosthodontic appliance, for example. A plurality of radio-opaque markers are temporarily secured directly to a patient's dentition. Surface data is then obtained, such as by scanning the patient's dentition with the markers or alternatively, by taking an impression of the patient's dentition with the markers, forming a physical model that includes analogs of the markers, and scanning the physical model. Either before or after the surface data is obtained, an anatomical, volumetric image data set of the patient's dentition is obtained via a volumetric scan of the patient's dentition with the markers appearing in the image data set. The markers appearing in both the volumetric data set and the surface data set are used by suitable computer software to merge the volumetric and surface data sets to form a merged image data set and to generate a combined model of the patient's dentition from which a surgical drill guide or other prosthodontic appliance may be designed and manufactured.

19 Claims, 4 Drawing Sheets

(56) References Cited

U.S. PATENT DOCUMENTS

| | | |
|---|---|---|
| 2007/0190481 A1 | 8/2007 | Schmitt |
| 2007/0190492 A1 | 8/2007 | Schmitt |
| 2011/0008751 A1* | 1/2011 | Pettersson .................... 433/167 |

* cited by examiner

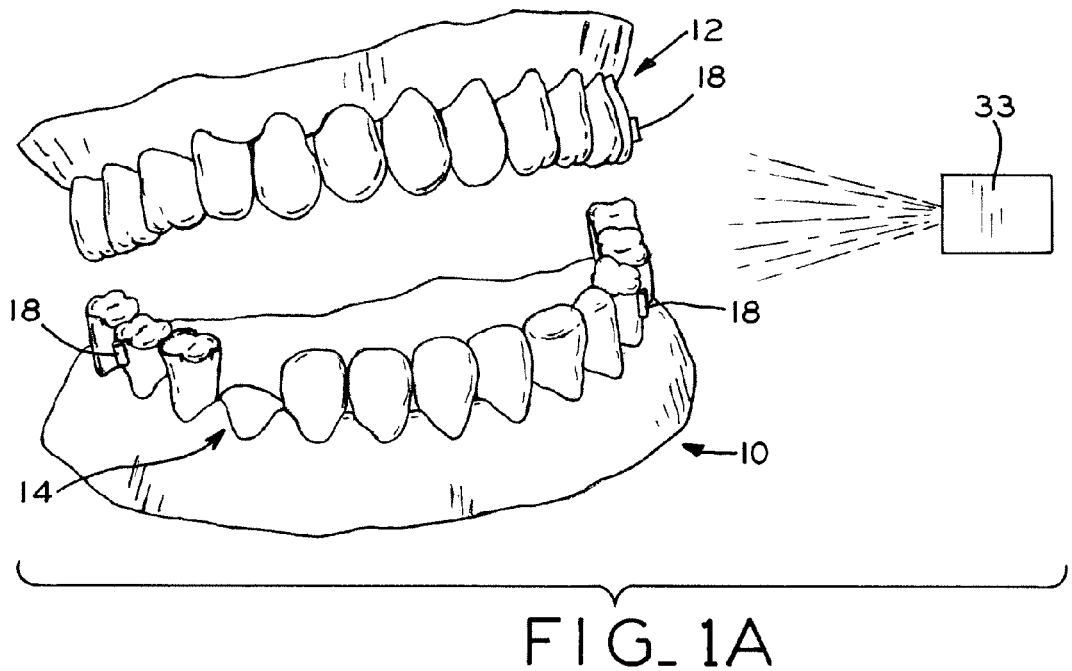
FIG_1A
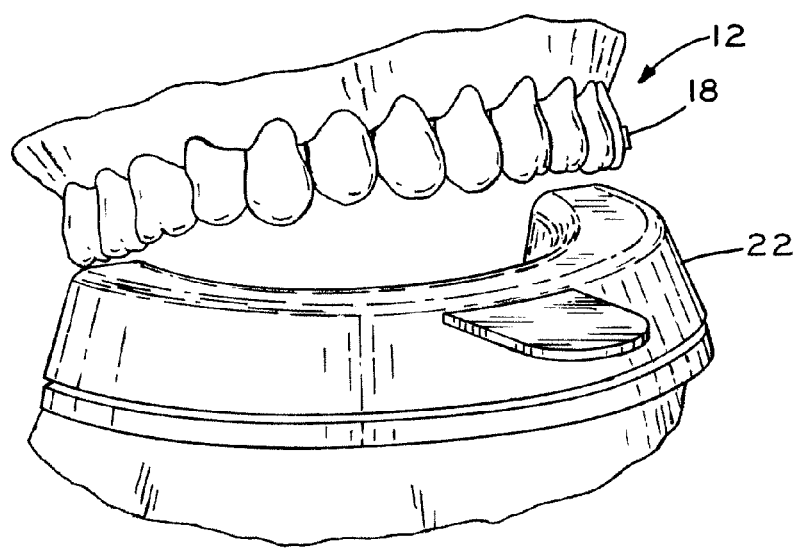
FIG_2

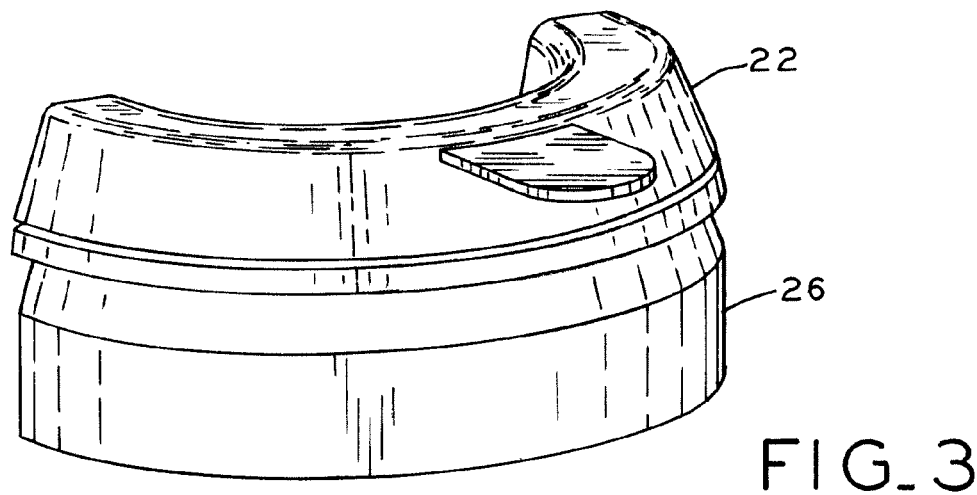
FIG_3
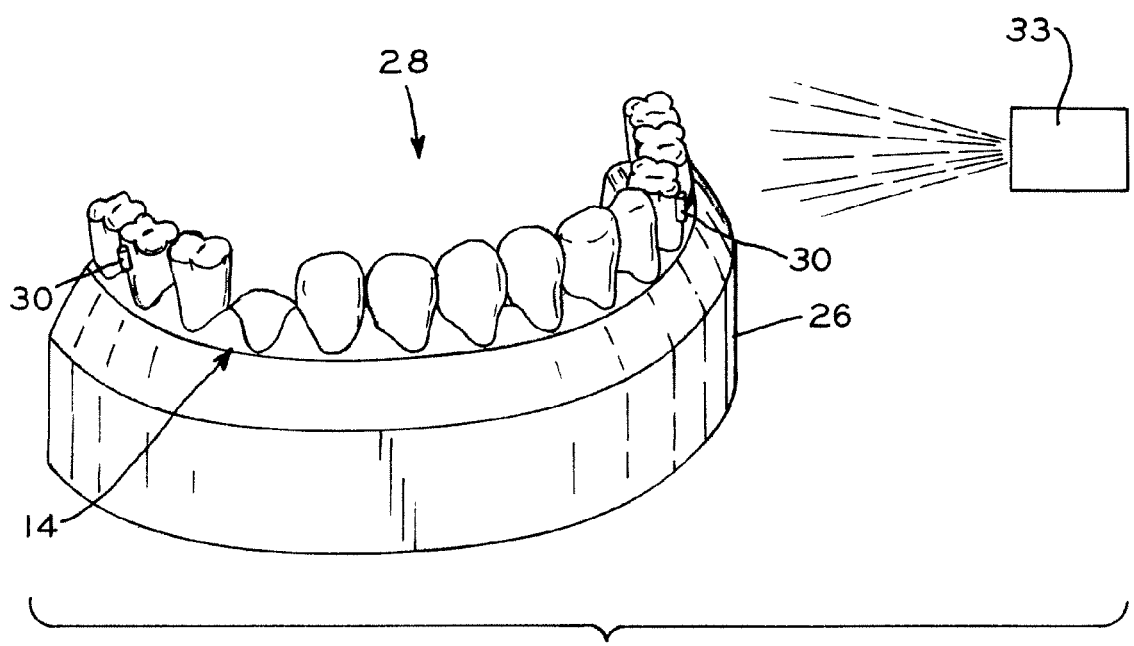
FIG_4

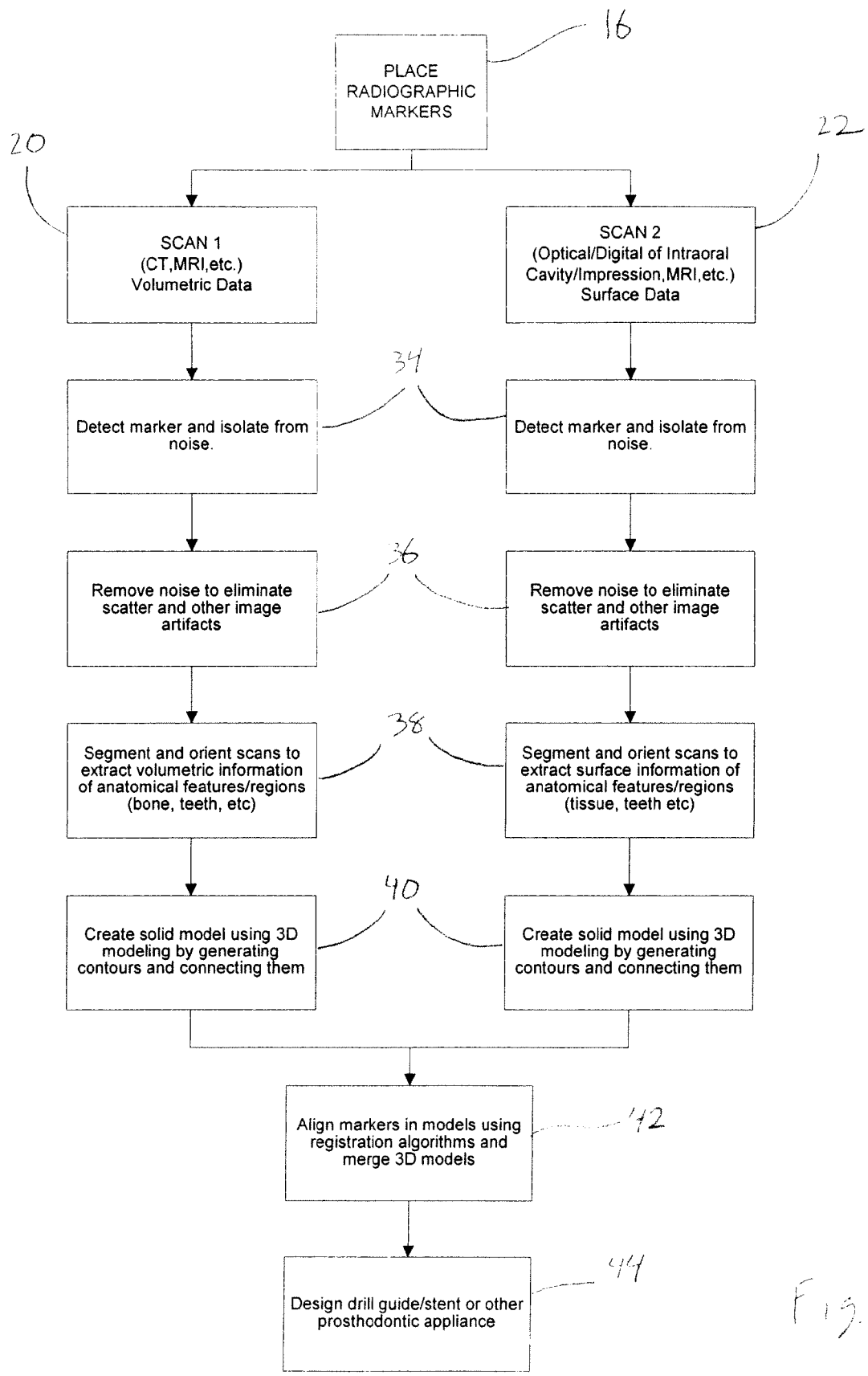

METHOD OF MERGING ANATOMICAL DATA AND SURFACE DATA OF A PATIENT'S DENTITION

CROSS REFERENCE TO RELATED APPLICATIONS

This application claims the benefit under Title 35, U.S.C. 119(e) of U.S. Provisional Patent Application Ser. No. 61/032,506, entitled METHOD OF MERGING ANATOMICAL DATA AND PHYSICAL MODEL DATA OF A PATIENT'S DENTITION, filed on Feb. 29, 2008, the disclosure of which is expressly incorporated by reference herein.

BACKGROUND OF THE INVENTION

1. Field of the Invention

The present invention relates to a method of obtaining and merging volumetric data and surface data of a patient's dentition for use in designing and/or manufacturing a prosthodontic component, such as a drill guide, implant, or other prosthodontic appliance, for example.

2. Description of the Related Art

Dental implants are commonly used as anchoring members in prosthodontic restorations to provide prosthetic teeth at one or more edentulous sites in a patient's dentition at which the patient's original natural teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods to replicate the shape of the tooth being replaced.

Many dental implant surgeries are performed in two stages. In the initial or first stage, an incision is made in the patient's gingiva at an edentulous side, and a bore is then drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around and/or into the implant to securely anchor the implant in the surrounding bone, a process known as osseointegration.

In a second stage of the procedure following osseointegration, the dentist surgically reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example.

If the patient has a site at which more than one tooth is missing, multiple implants may be used to provide anchorage for a denture bar, a bridge, or other prosthodontic appliance.

To drill holes in the jawbone of a patient, an oral surgeon may use a drill guide, which is typically formed as a custom appliance that overlays the drill site and at least a portion of the surrounding gum tissue and/or dentition. The drill guide includes a hole aligned along the intended drill axis, and one or more removable drill guide tubes may be positioned within the drill guide hole to allow drills of different diameters to be used in succession for drilling the holes in the jawbone in which the implants will be secured.

The drill guide may be fabricated based on a physical model of the patient's dentition, or may be designed based on scan data obtained of the patient's dentition.

In one procedure, an impression is taken of a patient's dentition during a first visit to the clinician. Then, at a dental lab, a physical model is made of the impression, and a waxed-up tooth or teeth may be made on the physical model at sites in which a patient's tooth or teeth are missing. In an edentulous patient, impressions may be taken of both the patient's existing dentures and of the patient's gum tissue without the dentures. Then, at the dental lab, a scan stent is made based on the impressions and/or the physical model. A least a portion of the scan stent typically corresponds to the patient's bite registration, and the scan stent also may include one or more structures corresponding to the waxed-up tooth or teeth. In an edentulous patient, the scan stent itself may resemble the patient's dentures.

The scan stent further includes radio-opaque markers that will appear in a radiographic scan, such as a computed tomography (CT) scan. A physical model scan is then obtained of the physical model with the scan stent placed on the physical model to generate image data corresponding to the exterior surfaces of the patient's teeth, soft tissue and gums. Then, the scan stent is shipped back to the clinician.

In a second visit to the clinician, the scan stent is placed within the patient's dentition, such as by fitting the stent directly on the patient's teeth or gums, or by the patient capturing the stent in between the patient's teeth, for example. A CT scan is then taken of the patient's dentition with the stent. The CT scan generates an image of the patient's jaw bone(s), teeth, and some of the surrounding soft tissue. However, in most cases in which the patient has had prior dental work, for example, the patient's amalgams, existing implants, or other metal structures cause scattering in the CT scan image such that the CT scan threshold must be set such that the CT scan only develops information corresponding to the jaw bone(s) and some of the surrounding soft tissue of the patient.

Therefore, in order for the clinician to properly plan the treatment, and for the lab technician to properly design the drill guide or other prosthodontic appliance, the images from both the physical model scan and from the anatomical CT scan must be merged to generate a combined image of the patient's dental condition that includes a more complete representation of the patient's bone, soft tissue, and teeth.

The radio-opaque markers of the scan stent that appear in each of the two scan images are used by suitable software to merge the scans, and a drill guide or other prosthodontic appliance is designed from the merged data.

Also, in many cases, a clinician may obtain a first, diagnostic CT scan of a patient in order to determine a treatment plan and, if the clinician determines that the patient is a good candidate for a suitable prosthetic appliance, the clinician will proceed as outlined above, including generating a later, second CT scan with the scan stent in place. Disadvantageously, this procedure requires two CT scans to be taken.

What is needed is a method that is an improvement on the foregoing.

SUMMARY OF THE INVENTION

The present invention provides a method of obtaining and merging volumetric data and surface data of a patient's dentition for use in designing and/or manufacturing a prosthodontic component, such as a drill guide, an implant, or other prosthodontic appliance, for example. A plurality of radio-opaque markers are temporarily secured directly to a patient's dentition. Surface data is then obtained, such as by scanning the patient's dentition with the markers or alternatively, by taking an impression of the patient's dentition with the markers, forming a physical model that includes analogs of the markers, and scanning the physical model. Either before or after the surface data is obtained, an anatomical, volumetric image data set of the patient's dentition is obtained via a volumetric scan of the patient's dentition with the markers appearing in the image data set. The markers appearing in both the volumetric data set and the surface data set are used by suitable computer software to merge the volumetric and surface data sets to form a merged image data set and to generate a combined model of the patient's dentition from which a surgical drill guide or other prosthodontic appliance may be designed and manufactured.

Advantageously, the present method obviates the need for a scan stent to be made, and also obviates the need for a patient to make two visits to a clinician, including a first visit in which an impression is taken from which a physical model and scan stent are made, and a second visit in which an anatomical scan is taken of the patient's dentition using the scan stent. Further, in instances in which the clinician desires a diagnostic CT scan, the clinician may first secure the markers to the patient's dentition prior to taking the CT scan and, if the clinician then determines that the patient is a good candidate for a prosthodontic appliance, the diagnostic CT scan may itself be used as the volumetric data set for case planning, thereby obviating the need to obtain two CT scans.

In one form thereof, the present invention provides a method for merging volumetric data and surface data of a patient's dentition, including the steps of attaching a plurality of radio-opaque markers to a patient's dentition; obtaining a volumetric data set of the patient's dentition, the volumetric data set including the radio-opaque markers; obtaining a surface data set, the surface data set including the radio-opaque markers; and merging the volumetric data set and the surface data set using the radio-opaque markers as common reference points.

In another form thereof, the present invention provides a method for merging volumetric data and surface data of a patient's dentition, including the steps of attaching a plurality of radio-opaque markers to a patient's dentition; obtaining a volumetric data set of the patient's dentition, the volumetric data set including the radio-opaque markers; making a physical model of the patient's dentition, the physical model including analogs of the radio-opaque markers; obtaining a surface data set from the physical model, the surface data set including the analogs of the radio-opaque markers; and merging the volumetric data set and the surface data set using the radio-opaque markers and the analogs of the radio-opaque markers as common reference points.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1A is a schematic view of a patient's dentition, showing a plurality of radio-opaque markers temporarily secured thereto, together with a scanning device;

FIG. 2 is a view showing an impression tray fitted about the lower arch of the patient's dentition;

FIG. 3 is a view of the impression tray of FIG. 2 fitted on a physical model base;

FIG. 4 is a view of a physical model of the patient's dentition, showing the analogs of the markers, together with a scanning device; and FIG. 5 is flow chart showing an overview of exemplary steps in the present method.

Corresponding reference characters indicate corresponding parts throughout the several views. The exemplification set out herein illustrates one embodiment of the invention, in one form, and such exemplification is not to be construed as limiting the scope of the invention any manner.

DETAILED DESCRIPTION

Figure 1B:
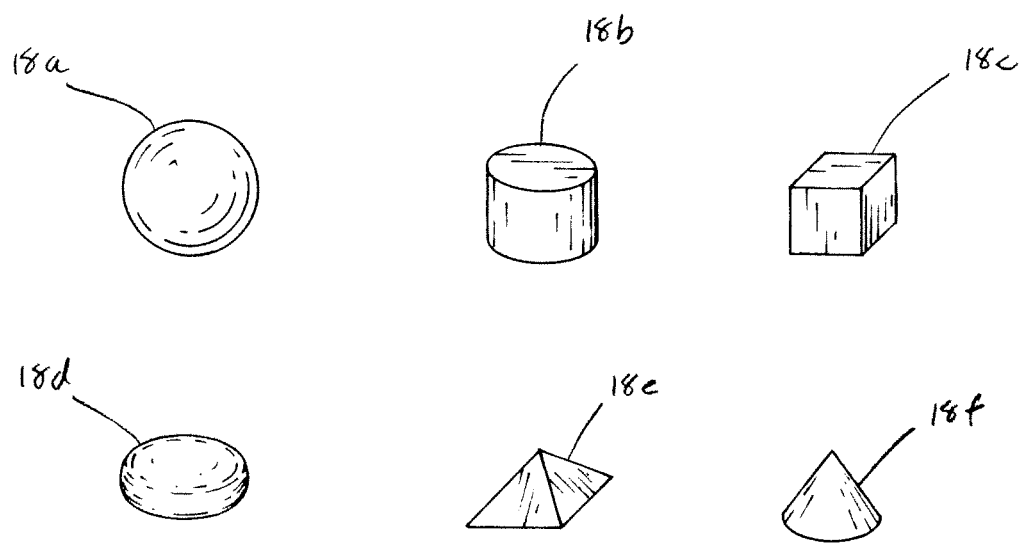
FIG. 1B are perspective views of representative shapes of the markers.

Referring to FIG. 1A, a patient's dentition is schematically shown, including lower or mandibular arch 10 and upper or maxillar arch 12. The patient's dentition may have one or more missing teeth as at site 14, or may be totally edentulous. At any location such as at site 14 in which the patient is missing one or more teeth, one or more holes may be drilled into the bone of the patient's arch to seat one or more implants (not shown) for osseointegration into the bone. A suitable prosthodontic component, such as an abutment (not shown) to which a crown (not shown) may be affixed, for example, is anchored by the implant. Alternatively, if more than one tooth is missing at site 14, a plurality of implants may be used to anchor another type of prosthodontic component, such as a denture bar or bridge structure, for example.

Referring additionally to FIG. 5, in a first step 16 of a method according to the present invention, one or more radio-opaque markers or fiducials 18 are temporarily secured to the patient's dentition. In one embodiment, a plurality of markers 18 are temporarily secured directly to the patient's teeth of the mandibular and/or maxillar arches 10, 12 using a suitable dental adhesive. In another embodiment, the markers may be fixed to the patient's gums via a suitable cement or by one or more sutures, for example, if the patient is edentulous. Markers 18 may be made of a radio-opaque material, such as titanium, stainless steel, other relatively dense biocompatible metals, a suitable plastic such as polyether ether ketone (PEEK), or gutta-percha, for example. Alternatively, a radio-opaque substance such as barium sulfate may be impregnated or integrated into a plastic material to form marker 18.

Referring to FIG. 1B, markers 18 may be shaped as a simple geometric shapes or volumes, such as sphere 18a, cylinder 18b, cube 18c, or ellipsoid 18d, pyramid 18e, or cone 18f for example, in order to provide a more accurate data set match, as described below. Exemplary markers 18 will be shown and described below as cylinders, although markers 18 have any of the foregoing shapes, or other shapes, may be used. Also, markers 18 having different shapes may be used together with a particular patient, for example, to aid in identifying certain anatomical features or regions of interest in the patient's dentition.

Referring to FIGS. 1 and 5, either before or after a surface data set is obtained, as described below, volumetric data is obtained of the patient's dentition in step 20 of FIG. 5, such as via an anatomical, volumetric radiographic scan of the patient's dentition ("SCAN 1" of FIG. 5) using a suitable medical imaging modality, including scanner 33 (FIG. 1A), to generate an anatomical data set or image(s) which includes the patient's dentition, markers 18, and the surrounding anatomical structures. Suitable medical imaging modalities include computed tomography (CT), magnetic resonance imaging (MRI), X-ray techniques, ultrasound imaging, or any other suitable medical imaging technique. The anatomical scan is primarily used to obtain data representative of the patient's jawbones, surrounding soft tissues, nerves, etc.

Either before of after the volumetric data is obtained, surface data is obtained of the patient's dentition in step 22 of FIG. 5 via another scan ("SCAN 2" of FIG. 5). The surface scan is primarily used to obtain data representative of the surfaces of the patient's teeth, soft tissue, and gums. A three-dimensional surface scan may be taken using a suitable optical scanner, digital scanner, laser scanner, three dimensional contact scanner, or any type of an active or passive non-contact scanner. In one embodiment, the surface data may be obtained via an intra-oral scan or via magnetic resonance imaging (MRI), designated by scanner 33 in FIG. 1A.

Alternatively, the surface data may be obtained by scanning a physical model of the patient's dentition. Referring to FIG. 2, an impression is taken of the mandibular and/or maxillar arch using a conventional impression tray 22 and impression material fitted about the arch. Thereafter, the impression tray 22 is removed from the arch with the impression material forming a negative representation of the patient's dentition. One advantage of using markers 18 that are shaped as simple geometric shapes is that markers 18 will tend to easily release from the impression material without tearing or otherwise damaging the impression material. Referring to FIGS. 3 and 4, a physical model, often referred to as a stone model, is made on a physical model base 26 from a material such as plaster using the impression tray and the impression material. The resulting physical model 28 is shown in FIG. 4, in which the radio-opaque markers 18 are represented as analogs 30 in the form of protrusions from the physical model 28. In an exemplary embodiment, analogs 30 will also be shaped as simple geometric shapes to allow for a more accurate data set match, as described below.

Then, in step 20 in FIG. 5 according to this alternative embodiment, physical model 28 is scanned using a suitable scanner 33 to generate the surface model image data set of the surfaces of the patient's dentition with the analogs 30. Typically, the physical model scan is primarily used to obtain data representative of the surfaces of the patient's teeth, soft tissue, and gums. As described above, a three-dimensional surface scan may be taken using a suitable optical scanner, digital scanner, laser scanner, three dimensional contact scanner, or any type of an active or passive non-contact scanner.

As discussed below with further reference to FIG. 5, the volumetric data set and the surface data set corresponding to the respective scan images may be processed to generate solid models, and the solid models may then be combined or merged with one another by suitable computer software/program using the radio-opaque markers 18 in the data sets as common reference or registration points between the models to form a combined or merged model that may be used to design a dental dill guide or prosthodontic implant or other appliance.

Suitable software for use in processing and merging the anatomical data set and the physical model data set includes Mimics® software, available from Materialise M.V., of Leuven, Belgium (Mimics® is a registered trademark of Materialise M.V.). The Materialise Mimics® software is an image processing package for 3-dimensional design and modeling, which generates and modifies surface 3D models from volumetric medical images such as Computed Tomography (CT) and Magnetic Resonance Imaging (MRI) through image segmentation in the STL format. Other similar software is available from 3Shape A/S of Copenhagen, Denmark.

Referring to FIG. 5, the acquired volumetric and surface data scans are pre-processed using noise-removal techniques to eliminate scatter and other image artifacts. In step 34, the markers 18 are identified in each scan and are isolated from surrounding image data and/or noise. Advantageously, when markers 18 are shaped as simple geometric shapes, the computer software may more easily identify markers 18 from the scan data representing the surrounding hard or soft tissues and/or noise in the scans, and the computer software will also be able to easily determine the center points of markers 18 using simple geometric formulas corresponding to the shapes of markers, which increases the accuracy of the subsequent merging of the volumetric data set and the surface data set.

In step 36, noise from the scans is removed to eliminate scatter and any other image artifacts. One source of potential scatter in the volumetric scan may be existing dental work in the patient's dentition, such as amalgams, existing implants, or other metal structures.

In step 38, the scan images are segmented to extract anatomical features or regions of interest, such as bone, tissue, teeth, etc., and to measure and display the features or regions of interest. Then, in step 40, the processed anatomical and physical scan images are individually stacked in the order of acquisition, and solid models of the dentition, jawbones, and soft tissue are developed from the scans using three-dimensional modeling techniques which generate and connect contours in the images.

In step 42, the two models generated form the volumetric and surface scans are superimposed using registration techniques. Registration establishes a common coordinate system for the separately developed models. When registering scans acquired from the same subject, the assumption that the body parts being imaged can be treated as a rigid body leads to a highly constrained spatial transformation model. The computer software identifies homologous structures, i.e., the markers 18, in the scans to be registered, and the mathematics for converting the markers 18 into an optimal spatial transformation is performed by calculating the transformation parameters.

A combined model of the patient's dentition is thus generated from the merger of the two models. This combined model may then be used by the clinician and/or lab technician to design, in step 44 of FIG. 5, a drill guide or other prosthodontic component using a computer aided design (CAD) program or other suitable software, with both the dentition and the surrounding anatomical structures, such as nerves, etc., of the patient viewable in the image in order to allow the clinician to take into account such structures in the design.

An example of a drill guide that may be designed with the present method is disclosed in U.S. Provisional Patent Application Ser. No. 61/092,900, entitled Dental Drill Guide System, filed on Aug. 29, 2008, assigned to the assignee of the present invention, the disclosure of which is incorporated by reference herein. An example of an abutment that may be designed with the present method is disclosed in U.S. patent application Ser. No. 11/362,236, entitled Ceramic/Metallic Dental Abutment, filed on Feb. 24, 2006, assigned to the assignee of the present invention, the disclosure of which is incorporated by reference herein.

The drill guide or other prosthodontic component may then be manufactured from biocompatible metal or plastic materials using material removal processes, such as computer aided machining (CAM) and/or milling, additive processes such as rapid prototyping, including stereolithography (SLA), selective laser sintering (SLS), fused deposition modeling (FDM), electron beam melting (EBM) or other techniques, or by formative methods such as molding or casting, for example.

Advantageously, the present method obviates the need for a scan stent to be made, and also obviates the need for a patient to make two separate visits to a clinician, including a first visit in which an impression is taken from which the physical model and scan stent are made, and a second visit in which an anatomical scan is taken of the patient's dentition using the scan stent. In the present method, the volumetric scan and the surface scan (or impression) may be obtained in the same visit, thereby reducing the number of visits to the clinician by alleviating the need for the patient to make a return trip to the clinician after a scan stent is made.

Further, when the clinician desires to first obtain a diagnostic CT scan of a patient's dentition, the clinician may first secure markers 18 to the patient's dentition prior to taking the diagnostic CT scan. If the clinician then determines that the patient is a good candidate for a prosthodontic appliance, the clinician may proceed as described above. In this manner, the diagnostic CT is itself used as the volumetric scan for case planning, thereby obviating the need to obtain two CT scans, namely, both a diagnostic CT scan and a volumetric, case-planning CT scan.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for merging volumetric data and surface data of a patient's dentition, comprising the steps of:
    attaching a plurality of radio-opaque markers to a patient's soft tissue;
    obtaining a volumetric data set of the patient's dentition, the volumetric data set including the radio-opaque markers attached to the patient's soft tissue;
    obtaining a surface data set of the patient's dentition, the surface data set including the radio-opaque markers attached to the patient's soft tissue; and
    merging the volumetric data set and the surface data set using the radio-opaque markers as common reference points.

2. The method of claim 1, wherein said obtaining a volumetric data set step is conducted prior to said obtaining a surface data set step.

3. The method of claim 1, wherein said obtaining a surface data set step is conducted prior to said obtaining a volumetric data set step.

4. The method of claim 1, wherein said obtaining a volumetric data set step comprises scanning the patient's dentition using a medical imaging modality.

5. The method of claim 1, wherein said obtaining a surface data set step comprises scanning the patient's dentition using a medical imaging modality.

6. The method of claim 1, wherein said obtaining a surface data set step comprises scanning the patient's dentition with an intra-oral scan.

7. A method for merging volumetric data and surface data of a patient's dentition, comprising the steps of:
    attaching a plurality of radio-opaque markers to a patient's soft tissue;
    obtaining a volumetric data set of the patient's dentition, the volumetric data set including the radio-opaque markers attached to the patient's soft tissue;
    obtaining a surface data set of the patient's dentition, by:
        taking an impression of at least a portion of the patient's dentition;
        making a physical model based on the impression; and
        scanning the physical model;
    wherein the surface data set includes the radio-opaque markers attached to the patient's soft tissue; and
    merging the volumetric data set and the surface data set using the radio-opaque markers as common reference points.

8. The method of claim 1, wherein in said attaching step, the markers have simple geometric shapes selected from the group consisting of spheres, cylinders, cubes, ellipsoids, pyramids, and cones.

9. A method for merging volumetric data and surface data of a patient's dentition, comprising the steps of:
    attaching a plurality of radio-opaque markers to a patient's soft tissue;
    obtaining a volumetric data set of the patient's dentition, the volumetric data set including the radio-opaque markers attached to the patient's soft tissue;
    making a physical model of the patient's dentition, the physical model including analogs of the radio-opaque markers attached to the patient's soft tissue;
    obtaining a surface data set from the physical model, the surface data set including the analogs of the radio-opaque markers attached to the patient's soft tissue; and
    merging the volumetric data set and the surface data set using the radio-opaque markers and the analogs of the radio-opaque markers as common reference points.

10. The method of claim 9, wherein said obtaining a volumetric data set step is conducted prior to said obtaining a surface data set step.

11. The method of claim 9, wherein said obtaining a surface data set step is conducted prior to said obtaining a volumetric data set step.

12. The method of claim 9, wherein said obtaining a volumetric data set step comprises scanning the patient's dentition using a medical imaging modality.

13. The method of claim 9, wherein said obtaining a surface data set step comprises scanning the physical model.

14. The method of claim 9, wherein said making a physical model step comprises:
    taking an impression of at least a portion of the patient's dentition; and
    making a physical model based on the impression.

15. The method of claim 9, wherein in said attaching step, the markers have simple geometric shapes selected from the group consisting of spheres, cylinders, cubes, ellipsoids, pyramids, and cones.

16. The method of claim 1, wherein in said attaching step, the markers are attached to a patient's gums.

17. The method of claim 1, wherein in said attaching step, the markers are attached to the patient's soft tissue using at least one suture.

18. The method of claim 9, wherein in said attaching step, the markers are attached to a patient's gums.

19. The method of claim 9, wherein in said attaching step, the markers are attached to the patient's soft tissue using at least one suture.

* * * * *